United States Patent
Ogawa et al.

[11] Patent Number: 5,886,198
[45] Date of Patent: Mar. 23, 1999

[54] METHOD FOR CONTINUOUSLY PRODUCING A CYCLIC FORMAL

[75] Inventors: Daisuke Ogawa; Masahiro Koike, both of Aichi; Yoshiyuki Yamamoto, Mie, all of Japan

[73] Assignee: Toray Industries, Inc., Japan

[21] Appl. No.: 13,840

[22] Filed: Jan. 27, 1998

[30] Foreign Application Priority Data

Jan. 29, 1997 [JP] Japan ................................ 9-015228
Aug. 7, 1997 [JP] Japan ................................ 9-213753

[51] Int. Cl.⁶ .................................................. C07D 307/04
[52] U.S. Cl. ............................ 549/430; 549/431; 568/724
[58] Field of Search .......................... 549/430, 431; 568/724

[56] References Cited

U.S. PATENT DOCUMENTS

3,857,759  12/1974  Fiore et al. .
5,456,805  10/1995  Thighpen .
5,616,736  4/1997  Thighpen .

Primary Examiner—Johann Richter
Assistant Examiner—Taofiq A. Solola
Attorney, Agent, or Firm—Austin R. Miller

[57] ABSTRACT

Cyclic formal is manufactured by cyclic reaction of an alkylene glycol and an aldehyde in a reactor, producing formal mixed with unreacted aldehyde as an impurity, which impurity is reduced in amount by connecting the reactor to a distillation tower and continuously supplying alkylene glycol to the distillation tower from which unreacted formaldehyde and a cyclic formal are being distilled, and continuously reacting them with supplied raw formaldehyde by countercurrent flow during distillation; water content in azeotropic admixture with cyclic formal can be removed by azeotropic distillation with a hydrocarbon azeotropic mixture with water, distilling water from the cyclic formal.

21 Claims, 2 Drawing Sheets

METHOD FOR CONTINUOUSLY PRODUCING A CYCLIC FORMAL

BACKGROUND OF THE INVENTION

The present invention relates to a method for continuously producing the compound cyclic formal, also sometimes known as methylal or dimethoxy methane, which is used as an intermediate in producing solvents and drugs, and as a raw material in production of acetal resin, etc., and related formal compounds such as ethylene glycol formal, diethylene glycol formal and 1,4-butanediol formal, for example. In more detail, the present invention relates to a method for continuously producing cyclic formal having reduced contents of impurities such as unreacted aldehyde or water.

It is known that cyclic alkylene formals such as ethylene glycol formal, diethylene glycol formal and 1,4-butanediol formal can be obtained by cyclic reaction between a corresponding alkylene glycol or alkylene oxide and aldehyde. For example, German Patent No. 191420 discloses a method for producing ethylene glycol formal, which is a typical cyclic formal, by reacting ethylene glycol and formaldehyde with each other in the presence of an acid catalyst.

Furthermore, Japanese Patent Laid-Open (Kokai) No. 49-62469 discloses a method for producing ethylene glycol formal by reacting ethylene glycol and paraformaldehyde in the presence of an acid catalyst.

Moreover, Japanese Patent Laid-Open (Kokai) No. 7-224055 discloses a method for obtaining a cyclic formal by reacting an alkylene glycol and formaldehyde with each other at a specific molar ratio.

Cyclic formals obtained by the above methods are usually obtained as a mixture of a cyclic formal containing a large amount of water, and water. Methods for decreasing water content in the mixture containing water, for obtaining a purified cyclic formal, are also known. For example, Japanese Patent Laid-Open (Kokai) No. 49-62469 discloses a method for producing a purified cyclic formal by adding cyclohexane to the reaction distillate obtained by reacting paraformaldehyde and ethylene glycol with each other in the presence of an acid catalyst, and rectifying the mixture. Japanese Patent Laid-Open (Kokai) No. 3-24071 discloses a purification method in which a crude cyclic acetal is treated with an aqueous alkali solution and/or a solid alkali hydroxide compound. Japanese Patent Laid-Open (Kokai) No. 5-241217 discloses a purification method in which the reaction distillate obtained by reacting formaldehyde and ethylene glycol in the presence of an acid catalyst is brought into contact with ethylene glycol in countercurrent flow in a distillation tower. Japanese Patent Laid-Open (Kokai) No. 7-206716 discloses a purification method in which a mixture containing a cyclic formal and water is brought into contact with a hydrophilic solvent having a boiling point of 180° to 250° C. in a distillation tower. Furthermore, Japanese Patent Laid-Open (Kokai) No. 7-206717 discloses a method in which the purified cyclic formal obtained in Japanese Patent Laid-Open (Kokai) No. 7-206716 is further treated with a dehydrating agent.

BRIEF SUMMARY OF THE INVENTION

However, the conventional methods for producing a cyclic formal still face practical problems yet unsolved. For example, if a cyclic formal is synthesized by reacting an alkylene glycol and formaldehyde, and the product containing the cyclic formal is removed from the reaction mixture, then the product contains unwanted unreacted formaldehyde. For this reason, these methods are commercially ineffective for producing a purified cyclic formal. The residual formaldehyde contained in the cyclic formal adversely affects the synthesis process and the subsequent purification process. For example, formaldehyde tends under various conditions to be converted into formic acid by Cannizzaro's reaction, corroding the synthesis equipment and complicating all of the other relevant equipment.

Because of these problems, in the production of a cyclic formal, it is desired to achieve a product that does not contain a significant amount of unreacted formaldehyde.

Conventional methods for purifying cyclic formal face other practical problems.

For example, in adding cyclohexane to a cyclic formal and rectifying the mixture, as in the aforementioned Kokai No. 5-241217, the decrease of water content tends not to be sufficient. Furthermore, in bringing a cyclic formal into contact with ethylene glycol or a hydrophilic solvent having a boiling point of 180° to 250° C. for distillation, though the water content of the cyclic formal decreases, water migrates into the ethylene glycol or into the hydrophilic solvent, and this requires further purification of the ethylene glycol or hydrophilic solvent. Therefore, the number of steps of the method increases and complicates the process disadvantageously, with the result that existing problems are not solved in a practically satisfactory manner. Accordingly, a process for producing a cyclic formal having reduced impurities, that is compatible with the synthesis process, and with purification of the cyclic formal, is needed.

We have studied intensively to find a method for continuously producing a cyclic formal having a large water content, but only a low content of unreacted formaldehyde, by reacting an alkylene glycol and formaldehyde and then distilling the resulting cyclic formal and its large water content for continuous purification. As a result, we have discovered that a cyclic formal having an acceptably low content of unreacted formaldehyde can be produced continuously by continuously supplying a raw alkylene glycol to a distillation tower from which unreacted formaldehyde and a cyclic formal are being distilled, and by continuously introducing raw formaldehyde to the reactor.

Furthermore, we have surprisingly found that a cyclic formal having low water content can be produced continuously by distilling the water-containing cyclic formal to continuously produce an azeotropic mixture of the cyclic formal and water, and adding to such azeotropic mixture a specific hydrocarbon compound capable of forming another azeotropic mixture with water, and conducting concurrent distillation of the two azeotropic mixtures. This is highly advantageously achieved in accordance with this invention.

OBJECTS OF THE INVENTION

An object of the invention is to provide a method for continuously producing a cyclic formal having only a small impurities content. A further object is to do this with a process consistent with the synthesis and purification of the cyclic formal.

Another object of the invention is to provide a method for producing a cyclic formal having radically reduced aldehyde and water contents.

A further object of the invention is to provide an easy and simple method for continuously producing a purified cyclic formal having only a small content of water, with highly improved rectification efficiency.

Still further objects of the present invention will become apparent from the following description.

BRIEF DESCRIPTION OF THE INVENTION

The present invention is directed to a method for continuously producing a cyclic formal, in which a reactor and a distillation tower are combined for reacting an alkylene glycol and formaldehyde with each other in the presence of a catalyst, and continuously distilling while supplying alkylene glycol from the distillation tower to the reactor portion, while also continuously supplying formaldehyde to that reactor, for reacting both the formaldehyde and the alkylene glycol with each other.

The present invention also relates to a method for continuously producing a cyclic formal, in which a reaction distillation tower is used to react countercurrently an alkylene glycol and formaldehyde with each other in the presence of a catalyst, to produce a cyclic formal. This is done by continuously supplying alkylene glycol from the distillation tower to the reactor portion of the reaction distillation tower while continuously supplying formaldehyde to the same reactor portion. Both the glycol and the formaldehyde react with each other, to continuously produce a reaction distillate containing water and a cyclic formal. By supplying the aforementioned reaction distillate containing water and the cyclic formal previously produced to a second distillation tower, to continuously produce an azeotropic mixture of the cyclic formal and water, and then supplying the azeotropic mixture to another azeotropic distillation tower, together with a selected hydrocarbon compound, the azeotropic point of which with water is equal to or lower than the boiling point of the cyclic formal, for continuous distillation, this produces an azeotropic mixture of the hydrocarbon and water with the cyclic formal at the top of the azeotropic distillation tower while continuously producing a cyclic formal having almost no water at the bottom of the second distillation tower.

Preferred embodiments of the invention are:

a. The alkylene glycol supplied to the distillation tower is brought into contact with the unreacted formaldehyde coming from the reactor in countercurrent flow, to absorb or react with previously unreacted formaldehyde, while being introduced into the reactor for reaction with the formaldehyde.

b. While the molar ratio of the alkylene glycol to formaldehyde in the reactor kept at about 1 or more, the amounts of alkylene glycol and formaldehyde continuously supplied to the distillation tower and the reactor are kept substantially equimolar.

c. The alkylene glycol is at least one glycol selected from the group consisting of ethylene glycol, diethylene glycol and 1,4-butanediol.

d. The reaction distillation tower used has two or more distillation stages in the distillation tower.

e. The distillation tower of the reaction distillation tower is a plate tower and/or a packed tower.

f. In the aforesaid azeotropic distillation step, the hydrocarbon compound is at least one cyclic compound selected from the group consisting of cyclopentane, cyclohexene and benzene.

g. In the same step, the azeotropic mixture consisting of a cyclic formal and water is supplied to the reflux portion or upper stage of the azeotropic distillation tower.

h. In the same step, the distillate from the azeotropic distillation tower is at least partially refluxed to the azeotropic distillation tower, without discharging all of the distillate outside the system.

This invention further relates to a dewatering method for continuously purifying a cyclic formal, in which method water is removed from a water-containing cyclic formal by distillation, comprising the step of adding a hydrocarbon compound, wherein the azeotropic boiling point of the hydrocarbon with water is not higher but preferably lower than the boiling point of the cyclic formal, to the water-containing cyclic formal, for continuous distillation. This continuous purification method includes the following preferable embodiments:

i. The cyclic formal is at least one selected from the group consisting of ethylene glycol formal, diethylene glycol formal and 1,4-butanediol formal.

j. The hydrocarbon compound is at least one selected from the group consisting of cyclopentane, cyclohexene and benzene.

k. The water-containing cyclic formal is supplied to the reflux portion or to an upper stage of the azeotropic distillation tower.

l. The distillate of the azeotropic distillation tower is at least partially refluxed to the distillation tower, without discharging all of the distillate outside the system at once.

DETAILED DESCRIPTION OF THE INVENTION

The alkylene glycols which can be used in the present invention include ethylene glycol, diethylene glycol, 1,2-propanediol, 1,3-propanediol, 1,4-butanediol, 1,5-pentanediol, 1,6-hexanediol, (hydromethoxy)ethanol, and others performing in the same way. Among them, ethylene glycol, diethylene glycol and 1,4-butanediol are especially preferable since they have high industrial utilization value. Ethylene glycol is especially preferable.

Formaldehyde, as the other reactant, can be a gas, an aqueous solution or can be present in a related compound such as formalin or paraformaldehyde or others, all of which are intended to be embraced by and included within the expression "formaldehyde." Because of ease of handling, a formaldehyde aqueous solution is especially preferable.

As the catalyst used in the present invention, an acid catalyst is suitable. The catalysts which can be used include mineral acids such as sulfuric acid and phosphoric acid, strong organic acids such as sulfonic acid, phosphonic acid and trifluoroacetic acid, solid acid catalysts such as strong acid cation exchange resins, zeolite, silica.alumina and activated clay, and heteropoly-acids such as phosphorus molybdic acid and phosphorus tungstic acid. As the catalyst, an acid that is nonvolatile under the existing reaction conditions is preferable.

Regarding the reaction distillation tower used in the aldehyde-glycol reaction, virtually any known reaction distillation tower can be used. For example, a conventional reaction distillation tower can be used with a distillation tower directly installed in a reactor. Alternatively, a separate reaction distillation tower can be used in which the distillate from a separate reactor is supplied to the bottom of the distillation tower by a pipe, or the like, while the condensate collected at the bottom of the distillation tower is returned to the reactor, also by a pipe or the like. The reaction distillation tower used in the practice of the present invention is not even limited to those described above.

Temperature control means for heating and cooling the aforementioned reactor and distillation tower can comprise any ordinary control means, such as steam, heating or cooling medium or electric heating, or any other suitable means.

The distillation tower for the aldehyde-glycol reaction can conveniently be a plate tower or a packed tower, for example, but is not limited to these. The plate type tower can be any type generally known or used in the art.

The packing in the packed tower, if used, can be of any type generally known or used in the art.

It is preferable that the number of distillation stages in the distillation tower of the reaction distillation tower is 2 or more. Simple distillation is operable but not preferable since the distilled cyclic formal contains a substantial amount of unreacted formaldehyde. If the number of distillation stages of the distillation tower is sufficiently great, operation can be conveniently effected without refluxing the condensate coming from the top of the distillation tower.

At the top of the distillation tower, a condenser can also be used to partially reflux the distillate, optimizing the function of distillation tower. Of course, the cyclic formal can also be produced without refluxing the distillate.

In the aldehyde-glycol reaction, the positions and timings for supplying the alkylene glycol and formaldehyde as raw materials to the reaction distillation tower are important. The alkylene glycol is supplied to the distillation tower and brought into contact with unreacted formaldehyde in countercurrent flow, for absorbing or reacting the glycol with the formaldehyde added to the reactor. On the other hand, it is important that the formaldehyde is directly supplied to the reactor for countercurrent contact of unreacted formaldehyde with the alkylene glycol. In this case, it is preferable to introduce the alkylene glycol to the distillation tower at a middle or higher stage of the distillation tower, to enhance the effect of countercurrent contact with the unreacted formaldehyde. However, the introductory position is not limited to a middle or higher stage, as far as a cyclic formal with a small unreacted formaldehyde content of, say, 1 wt % or less, preferably 0.5 wt % or less can be obtained as intended in the aldehyde-glycol reaction step.

In the aldehyde-glycol reaction step, it is preferable that the molar ratio of the alkylene glycol to the formaldehyde in the reactor is about 1 or more, more preferably about 2 or more. A molar ratio of less than 1 is operable but not preferable, since the unreacted formaldehyde content in the distilled cyclic formal becomes excessive. On the other hand, if the molar ratio of the alkylene glycol to formaldehyde in the reactor is very much larger, a correspondingly larger reactor is necessary. Therefore, industrially, it is preferable that the molar ratio of the alkylene glycol to formaldehyde is about 100 or less.

As for the amounts of the alkylene glycol and formaldehyde supplied to the distillation tower and the reactor in a steady continuous operation state, since they are consumed in approximately equimolar amounts, it is preferable to supply them in substantially equimolar amounts.

For reaction between the alkylene glycol and formaldehyde, ordinary reaction conditions can be adopted. For example, in the case of ethylene glycol formal, it is preferable that the reaction temperature is about 50° to 170° C., and a more preferable range is about 80° to 140° C. Furthermore, it is preferable that the reaction pressure may be controlled in the range of about atmospheric pressure to any suitable pressure at which an equimolar amount of water produced in the ethylene glycol-formal reaction and the water contained in the raw formaldehyde can be evaporated.

The vapor obtained in this reaction contains cyclic formal, water and unreacted formaldehyde. The reaction water, in an amount equal in moles to the cyclic formal, and the water in the formalin are distilled together. Thus, in this step, the cyclic formal is obtained as a mixture with a substantially equimolar amount of water produced in the reaction plus the water in the raw formalin (reaction distillate).

The resulting reaction distillate is subjected to distillation, but since the cyclic formal and water form an azeotropic mixture, it is difficult effectively to completely separate and remove the water from the formal by ordinary distillation only. Accordingly, the mixture of cyclic formal and water is transferred to a subsequent distillation step into which the azeotropic mixture consisting of the cyclic formal and water is introduced along with another azeotropic mixture of a selected different is hydrocarbon and water.

The subsequent distillation can be conducted in a conventional distillation tower.

As in the case of the distillation tower of the aldehyde-glycol step, if a plate tower is used, the plate type can be any type generally known or used in the art. If a packed tower is used, the packing can be of any type generally known or used in the art.

A distillation tower with a condenser installed at the top, for partially refluxing the distillate, can also be used.

The pressure of the subsequent distillation tower can be about atmospheric pressure, or at a higher pressure, or a reduced pressure. It is preferable that the temperature at the tower bottom is near the boiling point of water at the existing pressure, and that the temperature at the top of the azeotropic distillation tower is similarly near the azeotropic point of the cyclic formal and water at the existing pressure.

In order further to remove water from the azeotropic mixture consisting of the cyclic formal and water obtained in the aforesaid subsequent step, the azeotropic mixture consisting of the cyclic formal and water is supplied to the reflux portion or upper stage of the azeotropic distillation tower, while separately introducing a hydrocarbon compound to form another azeotropic mixture with water. The hydrocarbon may be introduced to a middle or higher stage of the azeotropic distillation tower. A purified cyclic formal can be obtained from the bottom of the azeotropic distillation tower.

It is important that the introduced hydrocarbon compound has an azeotropic vapor temperature with water of not higher than the boiling point of the cyclic formal. Suitable hydrocarbons for the purpose include cyclopentane, cyclohexene or benzene, or others. An especially preferable hydrocarbon compound for this purpose is benzene, which provides excellent separation efficiency between the cyclic formal and water.

As the hydrocarbon compound used to form an azeotropic mixture with water, the hydrocarbon compound obtained by condensing by a condenser, the hydrocarbon compound vapor containing water, etc. distilled from the top of the azeotropic distillation tower, and separating from the water phase of the condensate by a liquid-liquid separator can be refluxed to the azeotropic distillation tower.

Since the rectification in the hydrocarbon addition step is intended to separate water, the condensed and separated water phase is of course discharged outside the azeotropic distillation tower. However, if the water phase discharged outside the azeotropic distillation tower is at least partially returned to the azeotropic distillation tower, the rectification efficiency can be surprisingly improved.

As for the quantity of the distillate to be refluxed, it is only required that the molar ratio of the total quantity of the hydrocarbon compound used in circulation in the azeotropic distillation tower and newly supplied to it, to the total quantity of water used in circulation in the azeotropic distillation tower and newly supplied to it, is kept preferably at about 0.8 to 1.2. As a result, while the water content of the residue from the azeotropic distillation tower is desirably kept low, the accompanying hydrocarbon compound can be stably controlled.

It is preferable that if the distillate is refluxed it is refluxed substantially to a stage higher in the still than the stage to which the hydrocarbon compound is supplied, or that both are substantially supplied to the reflux portion. As a result, the azeotropic composition can be easily formed, preventing the water re-supplied in the distillate from being present in the residue.

In the present invention, it is preferable that the added amount of hydrocarbon compound used to form the aforesaid azeotropic mixture with water is about 0.1 to 10, expressed as a ratio by weight to the amount of the azeotropic mixture consisting of the cyclic formal and water. A more preferable range is about 0.5 to 5. Since the hydrocarbon compound accompanies the distillate coming from the top of the azeotropic distillation tower and the residue, the amount of the hydrocarbon compound to be newly supplied from outside corresponds approximately to the amount to make up for the shortage in the distillation tower. The amount of hydrocarbon compound to be newly supplied from outside is usually about 0.001 to 1, expressed as its ratio by weight to the amount of the azeotropic mixture consisting of cyclic formal and water.

The pressure within the azeotropic distillation tower for purifying the cyclic formal may be about atmospheric pressure, or a higher pressure, or a reduced pressure. It is preferable that the temperature at the tower bottom is at about the boiling point of the cyclic formal at the existing pressure, and that the temperature at the tower top is similarly about the azeotropic point of the hydrocarbon compound, cyclic formal and water at the existing pressure.

The azeotropic distillation tower used for purification may be any conventional distillation tower. If a plate tower is used, the plate type can be any type generally known or used in the art. If a packed tower is used, the packing can be of any type generally known or used in the art.

In the method of the present invention for continuously producing a purified cyclic formal, raw formaldehyde is preferably supplied to the reactor of the reaction distillation tower, and an alkylene glycol is preferably supplied to the distillation tower, to produce a cyclic formal with a small unreacted formaldehyde content. Furthermore, the cyclic formal with a small unreacted formaldehyde content is distilled, and rectified with a hydrocarbon solvent to form an azeotropic mixture with water. Thus, a cyclic formal having a small water content can be continuously and economically produced at a high yield. The method for continuously producing a cyclic formal of the present invention is economical and can be simplified in industrial operation very significantly.

DESCRIPTION OF THE PREFERRED EMBODIMENTS

The particular embodiments of the invention selected for illustration in the drawings are specific examples and are not intended to limit the scope of the invention, which is defined in the appended claims.

Figure 1:
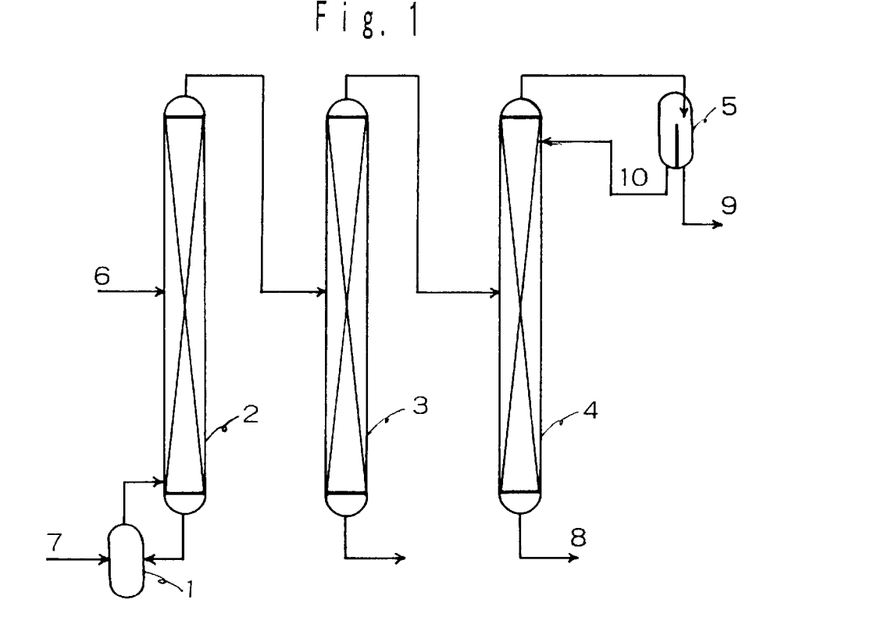
FIG. 1 is a schematic process drawing for illustrating one embodiment of a cyclic formal production process in accordance with the present invention.

In FIG. 1, a reactor 1 and a distillation tower 2 combine to perform the aldehyde-glycol reaction. As indicated by the arrows, the reactor 1 is connected to the distillation tower 2, and alkylene glycol is delivered from the bottom of the distillation tower 2 to the reactor 1. Furthermore, from the reactor 1, a glycol-formaldehyde product and an unreacted mixture are delivered to the distillation tower 2.

Predetermined amounts of an alkylene glycol, formaldehyde and catalyst are initially supplied into the reactor 1, and the temperature in the reactor 1 is increased to a predetermined level.

Formaldehyde is continuously supplied from an external feed or supply 7 into the reactor 1, and alkylene glycol is continuously supplied at 6 into the distillation tower 2, the pipe 6 here shown as being about midway up the tower 2.

The descending alkylene glycol supplied at 6 contacts the rising unreacted formaldehyde from the reactor 1 in countercurrent flow, to absorb it or react with it, while flowing down to the reactor 1. On the other hand, formaldehyde is directly supplied into the reactor 1, to contact unreacted formaldehyde with the alkylene glycol in countercurrent flow. In this case, for better countercurrent contact of both, it is preferable that the alkylene glycol is added at a middle or higher stage of the distillation tower 2.

The resulting formal tends to form an azeotropic mixture with any water that is present. Thus, a distillate can be obtained that is mainly alkylene glycol formal and water with only a small formaldehyde content. Furthermore, at the top of the distillation tower 2, a condenser (not illustrated) can also be installed to partially reflux the distillate.

Subsequently, this distillate is delivered to a second distillation tower 3 for continuous distillation. From the bottom of the second distillation tower 3, water is removed, and from the top of tower 3 an azeotropic mixture consisting of the alkylene glycol formal and water is delivered to an azeotropic distillation and purification tower 4, as shown in FIG. 1. Separately, a selected hydrocarbon compound such as benzene, for example, is continuously fed into the top of the azeotropic distillation tower 4, for distillation in the azeotropic distillation tower 4.

In this case, a vapor is taken out from the top of the azeotropic distillation tower 4, condensed by a condenser (not illustrated), and separated into a hydrocarbon compound phase and a water phase in a liquid-liquid separator 5. The hydrocarbon compound is continuously supplied to the top of the azeotropic distillation tower 4 through a reflux pipe 10. From the bottom of the liquid-liquid separator 5, the aqueous phase is removed through a distillation drain 9 provided for removal of condensate. From the residue collecting portion at the bottom of the azeotropic distillation tower 4 the purified and dewatered alkylene glycol formal product is removed through product line 8.

Figure 2:
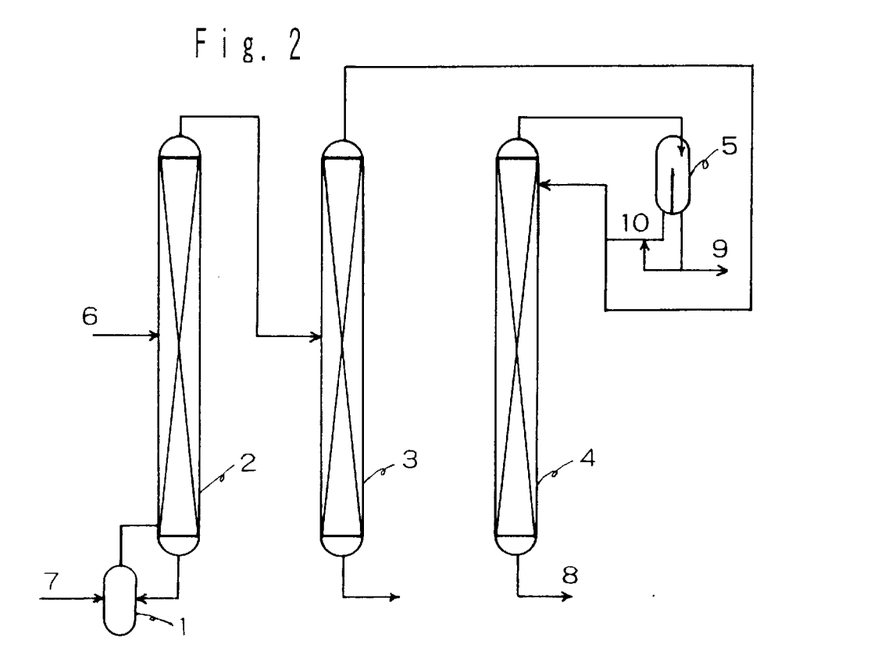
FIG. 2 is a schematic process drawing illustrating another embodiment of cyclic formal production process in accordance with the present invention.

FIG. 2 shows another embodiment of the invention, using the same identification numbers as those used in FIG. 1. The azeotropic formal-water mixture from the top of distillation tower 3 is continuously supplied to the reflux line 10 of the azeotropic distillation tower 4 as shown in FIG. 2. Separately, the selected hydrocarbon compound such as benzene, for example, is also continuously supplied through the reflux line 10 to the azeotropic distillation tower 4. The vapor taken out of the top of the azeotropic distillation tower 4 is condensed by a condenser (not illustrated) and separated into a hydrocarbon compound phase and a water phase in the liquid-liquid separator 5. The resulting hydrocarbon compound is continuously supplied through the reflux pipe 10 to the top of the azeotropic distillation tower 4.

From the bottom of the liquid-liquid separator 5, the aqueous phase material is removed through the drain 9. The condensed and separated aqueous phase is mainly discharged outside the system, but as illustrated in FIG. 2, it may at least partially be returned to the azeotropic distillation tower 4 through the line 10. Thus, the rectification efficiency can be significantly improved. As in FIG. 1, the product line 8 at the bottom of the azeotropic distillation tower 4 collects and delivers the purified and dewatered alkylene glycol formal.

Figure 3:
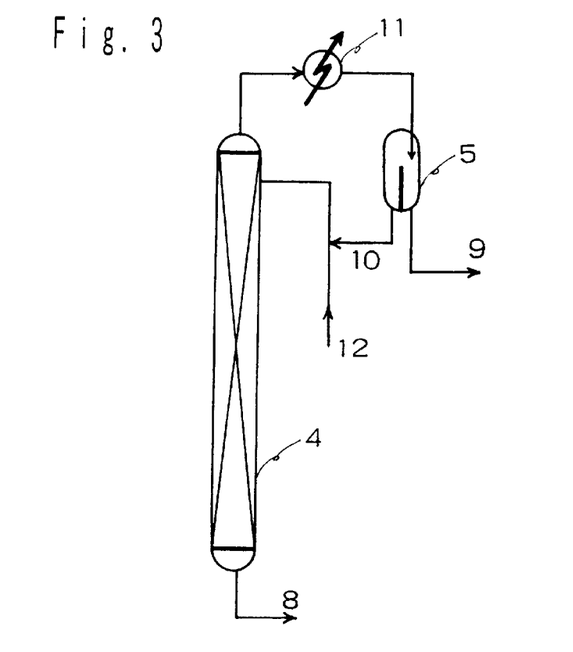
FIG. 3 is a schematic process drawing showing a modified azeotropic distillation column of the apparatus of FIGS. 1 and 2, illustrating a further purification process in accordance with the present invention.

In FIG. 3 the azeotropic mixture of alkylene glycol formal and water produced in accordance with either of FIGS. 1 and 2 (not shown in FIG. 3) is continuously supplied to the reflux line of the azeotropic distillation tower 4 shown in FIG. 3. Separately the hydrocarbon compound is also continuously supplied through the reflux line 12 to the azeotropic distillation tower 4. Subsequently, the vapor taken out of the top of the azeotropic distillation tower 4 is condensed by a condenser 11, and is separated into a hydrocarbon phase and an aqueous phase by the liquid-liquid separator 5. The obtained hydrocarbon compound is continuously supplied to the top of the azeotropic distillation tower 4 through the reflux pipe 10.

In this case, to make up for the decreased hydrocarbon compound in the azeotropic distillation tower 4, the hydrocarbon compound can be additionally supplied from a separate hydrocarbon compound supply line 12. From the residue portion at the bottom of the azeotropic distillation tower 4, the purified alkylene glycol formal is removed through the product line 8, as before.

Figure 4:
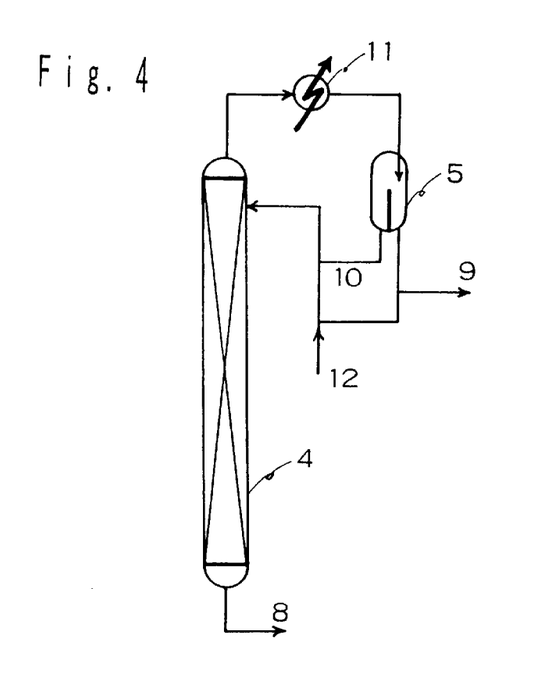
FIG. 4 is a schematic process drawing showing a modified azeotropic distillation portion of the apparatus of FIGS. 1 and 2, illustrating a still further modification of the purification process according to the present invention.

FIG. 4 shows a still further embodiment of the azeotropic distillation tower 4. The azeotropic mixture of alkylene glycol formal and water is continuously supplied to the azeotropic distillation tower 4 through the reflux line 10 of the azeotropic distillation tower 4 shown in FIG. 4, as described before. Furthermore, the selected hydrocarbon compound is also continuously supplied to the azeotropic distillation tower 4 through the reflux line 10. Subsequently, the vapor taken out of the top of the azeotropic distillation tower 4 is condensed by the condenser 11 and separated into a hydrocarbon compound phase and a water phase in the liquid-liquid separator 5. The hydrocarbon compound is continuously supplied at or near the top of the azeotropic distillation tower 4 through the reflux pipe 10. In this case, to make up for the decreased hydrocarbon compound in the azeotropic distillation tower 4, the hydrocarbon compound can be additionally supplied through the reflux pipe 10 through the hydrocarbon compound supply line 12. Furthermore, the water phase condensed and separated in the liquid-liquid separator 5 is discharged outside the system, but as illustrated, some of it can be returned to the azeotropic distillation tower 4, to significantly improve the rectification efficiency. From the collecting chamber at the bottom of the azeotropic distillation tower 4, the purified alkylene glycol formal is removed through the line 8, as before.

EXAMPLES

Examples of the present invention are described below. The present invention is not limited thereto or thereby, and can be properly modified within the scope of the present invention.

Example 1

In this example, as in FIG. 1, a reaction distillation apparatus consisting of a reactor 1 (with a capacity of 800 ml) connected to a distillation tower 2, which was an Older Shaw plate tower with a diameter of 30 mm and 20 sieve trays installed.

At first, 270 g (4.4 moles) of ethylene glycol, 130 g of 60% formalin (2.6 moles of formaldehyde) and 4 g of sulfuric acid were initially supplied into the reactor 1, and the reactor 1 was heated to an inside temperature of 120° C. Sixty percent formalin was continuously supplied to the reactor 1 from the formalin supply line 7, at a rate of 85 g/hr (1.7 moles of formaldehyde per hour). Separately, ethylene glycol was continuously supplied through the supply port 6, located at the 10th stage from the bottom of the distillation tower 2. Its flow rate was 106 g/hr (1.7 moles/hr).

The ethylene glycol to be supplied to the distillation tower 2 descended into the reactor 1 by countercurrent flow against the ascending formaldehyde and reaction product coming from the reactor 1, for further reaction with the unreacted formaldehyde.

In the reaction distillation tower 2, it took 120 minutes to obtain a distillate with a stable composition (reaction distillate). The distillate was analyzed by gas chromatography and found to contain 65.4 wt % of ethylene glycol formal, 33.7 wt % of water and 0.1 wt % of formaldehyde.

Example 2

Ethylene glycol formal was produced as described in Example 1, except that the amounts of ethylene glycol and 60% formalin initially supplied into the reactor 1 were 140 g (2.3 moles) of ethylene glycol and 200 g of 60% formalin (4 moles of formaldehyde). The obtained distillate (reaction distillate) was analyzed by gas chromatography and found to contain 62.8 wt % of ethylene glycol formal, 33.1 wt % of water and 1.0 wt % of formaldehyde.

It can be seen that if the molar ratio of ethylene glycol to formaldehyde in the reactor 1 is larger than 1, the amount of formaldehyde present as an impurity in the ethylene glycol formal is small.

Example 3

The reaction distillation tower 2 of FIG. 1 was connected as that of Example 1 except that the distillation tower 2 was a packed tower with a diameter of 30 mm, two distillation stages and ring type packing.

Two hundred and seventy grains (4.4 moles) of ethylene glycol, 130 g of 60% formalin (2.6 moles of formaldehyde) and 4 g of sulfuric acid were initially supplied into the reactor 1, and the reactor was heated to 110° C. When the inside temperature of the reactor 1 reached 120° C. 60% formalin was continuously supplied into the reactor 1 at a flow rate of 85 g/hr (1.7 moles of formaldehyde per hour), and ethylene glycol was continuously supplied to the 1st stage from the bottom of the distillation tower 2 at a flow rate of 106 g/hr (1.7 moles/hr).

In the reaction distribution tower, it took 120 minutes to obtain a distillate with a stable composition (reaction distillate). The distillate was analyzed by gas chromatography and found to contain 64.3 wt % of ethylene glycol formal, 33.4 wt % of water and 0.5 wt % of formaldehyde.

Example 4

The reaction distillation tower consisted of a reactor 1 (FIG. 1) (with a capacity of 800 ml) and a distillation tower 2 (Older Shaw plate tower with a diameter of 30 mm and 20 sieve trays installed) connected as shown in FIG. 1.

Two hundred and seventy grams (4.4 moles) of ethylene glycol, 130 g of 60% formalin (2.6 moles of formaldehyde) and 4 g of sulfuric acid were initially supplied into the reactor 1, and the reactor 1 was heated to an inside temperature of 120° C. When the inside temperature of the reactor 1 reached 120° C. 60% formalin was continuously supplied from the formalin supply port 7 into the reactor 1 at a flow rate of 85 g/hr (1.7 moles of formaldehyde per hour), and ethylene glycol was continuously supplied from the ethylene glycol supply port 6 at the 10th stage from the bottom of the distillation tower 2 at a flow rate of 106 g/hr (1.7 moles/hr).

It took 120 minutes to obtain a distillate with a stable composition (reaction distillate). The distillate was analyzed by gas chromatography and found to contain 65.4 wt % of ethylene glycol formal, 33.7 wt % of water and 0.1 wt % of formaldehyde.

In succession, the distillate was supplied into the distillation tower 3 of FIG. 1 (plate tower with a diameter of 30 mm and 20 sieve trays) at the 10th stage above the bottom of the distillation tower 3 at a flow rate of 191 g/hr, for continuous distillation at a tower bottom temperature of 103° C. It took 120 minutes to obtain a distillate with a stable composition. From the top of the second distillation tower 3, an azeotropic mixture containing 91.8 wt % of ethylene glycol formal and 7.6 wt % of water was obtained.

This azeotropic mixture was continuously supplied to the 10th stage above the bottom of the azeotropic distillation tower 4 (FIG. 1) (plate tower with a diameter of 30 mm and 40 sieve trays) for purification shown in FIG. 1 at a flow rate of 136/hr, and benzene as the selected hydrocarbon was continuously supplied to the 3rd stage from the top of the azeotropic distillation tower 4 at a flow rate of 16 g/hr. The distillation operation in the azeotropic distillation tower 4 was conducted at atmospheric pressure at a tower bottom temperature of 77° C. Subsequently, the vapor from the tower top was condensed and separated into a benzene phase and a water phase in the liquid-liquid separator 5, and the benzene phase was continuously supplied to the 1st stage from the top of the azeotropic distillation tower 4 at a flow rate of 367 g/hr.

From the product collecting portion 8 at the tower 4 bottom, purified ethylene glycol formal containing 11 wt % of benzene was obtained at 135 g/hr. The yield of ethylene glycol formal to the initially supplied ethylene glycol and formaldehyde was 97.5%. The water content was measured according to the known Karl Fischer method and found to be only 44 ppm.

Example 5

The azeotropic mixture obtained in Example 4 (containing 91.8 wt % of ethylene glycol formal and 7.6 wt % of water) was continuously supplied into the reflux line 10 of the azeotropic distillation tower 4 (plate tower with a diameter of 30 mm and 40 sieve trays) for purification as shown in FIG. 2 at a flow rate of 136 g/hr, and benzene was also continuously supplied as the selected hydrocarbon into the reflux line 10 at a flow rate of 16 g/hr. The azeotropic distillation tower 4 was operated at atmospheric pressure at a tower bottom temperature of 77° C. Subsequently, the vapor taken out of the top of the azeotropic distillation tower 4 was condensed and separated into a benzene phase and a water phase in the liquid-liquid separator 5, and the benzene was continuously supplied to the 1st stage from the tower top through the line 10 at a flow rate of 367 g/hr. Furthermore, a supply of water was provided and gradually increased and eventually water was continuously supplied to the top of the azeotropic distillation tower 4 at a flow rate of 9 g/hr. From the product line 8 at the tower bottom, purified ethylene glycol formal containing 0.7 wt % of benzene was collected at 135 g/hr. The yield of ethylene glycol formal to the initially supplied ethylene glycol and formaldehyde was 97.5%. The water content was measured according to the Karl Fischer method and found to be only 22 ppm.

Comparative Example 1

Ethylene glycol formal was produced as described in Example 4, except that ethylene glycol was supplied together with formaldehyde into the reactor, instead of supplying ethylene glycol to the 10th stage from the bottom of the distillation tower 2. It was analyzed as described in Example 4 and found to contain 63.4 wt % of ethylene glycol formal, 33.8 wt % of water and 1.8 wt % of formaldehyde. It can be seen that the product of the present invention as illustrated by Examples 1–4 is significantly superior in reduction of content of aldehyde as an impurity in ethylene glycol formal.

The distillate was dewatered in the azeotropic distillation tower 4 after distillation in the second distillation tower as described in Example 4. The yield of ethylene glycol formal was 91.4%, and the water content measured according to the Karl Fischer method was 46 ppm.

Comparative Example 2

Ethylene glycol formal was produced as described in Example 1, except that methanol was introduced as the selected organic compound (not a hydrocarbon) into the azeotropic distillation tower 4 instead of benzene. In this case, the yield of ethylene glycol formal was 97.0%. The water content was measured by gas chromatography and found to be 6.5 wt %.

Example 6

A reaction distillation tower consisting of a reactor with a capacity of 800 ml and a distillation tower 2 (plate tower with a diameter of 30 mm and 20 sieve trays) shown in FIG. 1 was used.

Two hundred and seventy grams (4.4 moles) of ethylene glycol, 130 g of 60% formalin (2.6 moles of formaldehyde) and 4 g of sulfuric acid were initially supplied into the reactor, and the reactor 1 was heated until the inside temperature reached 120° C. When the inside temperature of the reactor 1 reached 120° C. 60% formalin was continuously supplied into the reactor 1 at a flow rate of 85 g/hr (1.7 moles of formaldehyde per hour), and ethylene glycol was continuously supplied into the distillation tower 2 at a flow rate of 106 g/hr (1.7 moles/hr), for operation at a reflux ratio of 0.5. It took 120 minutes to obtain a distillate with a stable composition (reaction distillate). The distillate was analyzed by gas chromatography and found to contain 65.4 wt % of ethylene glycol, 33.7 wt % of water and 0.1 wt % of formaldehyde. The distillate was supplied into the second distillation tower 3 (plate tower with a diameter of 30 mm and 20 sieve trays), heated to 74° C. at atmospheric pressure, and distilled at a reflux ratio of 0.6, to obtain an azeotropic mixture containing 91.8 wt % of ethylene glycol formal and 7.6 wt % of water from the top of the second distillation tower.

The azeotropic mixture containing ethylene glycol formal and water was continuously supplied to the 10th stage from the bottom of the azeotropic distillation tower (plate tower with diameter of 30 mm and 40 sieve trays) shown in FIG. 1 at a flow rate of 211 g/hr, and benzene was continuously supplied as the selected hydrocarbon to the 3rd stage from the tower top at a flow rate of 24 g/hr, for operation at atmospheric pressure at a tower bottom temperature of 77° C. Then, the vapor from the tower top was condensed and separated into a benzene phase and a water phase in the liquid-liquid separator, and the benzene phase was continuously supplied to the top of the azeotropic distillation tower at a flow rate of 570 g/hr. Purified ethylene glycol formal was obtained from the tower bottom. When measured according to the aforementioned Karl Fischer method, the water content was found to be 40 ppm and the benzene content was found to be 12 wt %.

Example 7

The azeotropic mixture containing 91.8 wt % of ethylene glycol formal and 7.6 wt % of water obtained in Example 6 was continuously supplied into the reflux line of the azeotropic distillation tower 4 (plate tower with a diameter of 30 mm and 40 sieve trays) shown in FIG. 3 at a flow rate of 211 g/hr, and benzene was also continuously supplied to the reflux line at a flow rate of 24 g/hr, for operation at atmospheric pressure at a tower bottom temperature of 77° C. Subsequently, the vapor from the top of the azeotropic distillation tower 4 was condensed and separated into a benzene phase and a water phase in the liquid-liquid separator 5, and the benzene phase was continuously supplied to the top of the azeotropic distillation tower 4 at a flow rate of 570 g/hr. From the bottom of the azeotropic distillation tower 4, purified ethylene glycol formal was collected. When measured according to the Karl Fischer method, the water content was found to be only 20 ppm and the benzene content was found to be 12 wt % as before.

Example 8

The azeotropic mixture containing 91.8 wt % of ethylene glycol formal and 7.6 wt % of water obtained in Example 6 was continuously supplied into the reflux line of the azeotropic distillation tower 4 (plate tower with a diameter of 30 mm and 40 sieve trays) shown in FIG. 4 at a flow rate of 211 g/hr, and benzene was also continuously supplied into the reflux line at a flow rate of 24 g/hr, for operation at atmospheric pressure at a tower bottom temperature of 77° C. Subsequently, the vapor from the tower top was condensed by the condenser 11 and separated into a benzene phase and a water phase in the liquid-liquid separator 5, and the benzene phase was continuously supplied to the top of the azeotropic distillation tower 4 at a flow rate of 570 g/hr. Furthermore, supply of a water phase was gradually started, and finally water was continuously supplied to the tower top at a flow rate of 14 g/hr. When the distillate and the residue of the azeotropic distillation tower 4 became stable in composition, purified ethylene glycol formal was obtained from the bottom of the azeotropic distillation tower 4. When measured according to the Karl Fischer method, the water content was found to be only 20 ppm and the benzene content was found to be 0.8 wt %.

What is claimed is:

1. A method for continuously producing a cyclic formal from an alkylene glycol and an aldehyde, in which a reaction distillation tower is provided comprising a distillation tower that is connected to or integral with a reactor and provided for reacting said alkylene glycol and said aldehyde to produce said cyclic formal, the step which comprises:
    (a) conducting said alkylene glycol into and from said distillation tower to said reactor while continuously supplying said aldehyde to said reactor, for reacting both said alkylene glycol and said aldehyde.
2. The method according to claim 1, wherein said aldehyde is formaldehyde and wherein said reaction produces a cyclic formal product containing unreacted formaldehyde, the steps of reducing the content of said unreacted formaldehyde in said formal product, which steps comprise:
    bringing said alkylene glycol supplied to said distillation tower into countercurrent contact with said cyclic formal product containing unreacted formaldehyde coming from said reactor, to absorb or react said alkylene glycol with said unreacted formaldehyde in said cyclic formal product, by countercurrent reaction of said alkylene glycol with said unreacted formaldehyde.
3. The method according to claim 1, wherein the molar ratio of said alkylene glycol to aldehyde in said reactor is controlled to about 1 or more, while the amounts of said alkylene glycol and said aldehyde continuously supplied into said distillation tower and said reactor are substantially equimolar.
4. The method according to claim 2, wherein the molar ratio of said alkylene glycol to formaldehyde in said reactor is controlled to about 1 or more, while the amounts of said alkylene glycol and said formaldehyde continuously supplied into said distillation tower and said reactor are substantially equimolar.
5. The method according to claim 3, wherein said alkylene glycol is at least one glycol selected from the group consisting of ethylene glycol, diethylene glycol and 1,4-butanediol.
6. The method according to claim 4, wherein said alkylene glycol is at least one glycol selected from the group consisting of ethylene glycol, diethylene glycol and 1,4-butanediol.
7. The method according to claim 1, wherein said reaction distillation tower has two or more distillation stages.
8. The method according to claim 1, wherein said distillation tower is a plate tower and/or a packed tower.
9. A method for continuously producing a cyclic formal in a reaction distillation tower apparatus which comprises a reactor and a distillation tower connected together to react an alkylene glycol and formaldehyde with each other in the presence of a catalyst, to produce a cyclic formal, the steps which comprise:
    (1) feeding alkylene glycol and formaldehyde into said reactor to produce formal and unreacted formaldehyde in said reactor,
    (2) continuously supplying alkylene glycol to said distillation tower at a location spaced above its bottom,
    (3) continuously supplying formaldehyde to said reactor for reacting said alkylene glycol and said formaldehyde with each other and delivering the reaction product to a lower portion of said distillation tower,
    (4) continuously producing a reaction distillate from an upper portion of said distillation tower containing water and a cyclic formal,
    (5) continuously supplying said reaction distillate containing water and a cyclic formal from said step (1) to a second distillation tower, to continuously produce an azeotropic mixture of said cyclic formal and water, and (6) supplying said azeotropic mixture obtained in said step (2) to an azeotropic distillation tower while supplying thereto a hydrocarbon compound having an azeotropic point with water which is equal to or less than the boiling point of said cyclic formal, for continuous distillation, and (7) said azeotropic mixture comprising said hydrocarbon and water from an upper top portion of said azeotropic distillation tower while continuously producing dewatered cyclic formal from a lower portion of said azeotropic distillation tower.

10. The method according to claim 9, wherein the molar ratio of said alkylene glycol to said formaldehyde in said reactor is maintained at about 1 or more, and wherein the amounts of said alkylene glycol and said formaldehyde continuously supplied into said distillation tower and said reactor are substantially equimolar.

11. The method according to claim 9, wherein said alkylene glycol is at least one glycol selected from the group consisting of ethylene glycol, diethylene glycol and 1,4-butanediol.

12. The method according to claim 9, wherein said hydrocarbon compound is selected from the group consisting of cyclopentane, cyclohexene and benzene.

13. The method according to claim 10, wherein said hydrocarbon compound is selected from the group consisting of cyclopentane, cyclohexene and benzene.

14. The method according to claim 11, wherein said hydrocarbon compound is selected from the group consisting of cyclopentane, cyclohexene and benzene.

15. The method according to claim 9, wherein said azeotropic mixture of said cyclic formal and water is supplied to the reflux portion or upper stage of said azeotropic distillation tower.

16. The method according to claim 9, wherein the distillate from said azeotropic distillation tower is refluxed at least partially to said azeotropic distillation tower, without discharging all of said distillate outside the system.

17. The method in which water is removed from a cyclic formal containing water by distillation, the step of:

adding a hydrocarbon compound, the azeotropic point of which with water is equal to or lower than the boiling point of said cyclic formal, to said cyclic formal containing water, for continuous distillation.

18. The method according to claim 17, wherein said cyclic formal is at least one formal selected from a group consisting of ethylene glycol formal, diethylene glycol formal and 1,4-butanediol formal.

19. The method according to claim 17, wherein said hydrocarbon compound is at least one hydrocarbon selected from the group consisting of cyclopentane, cyclohexene and benzene.

20. The method according to claim 17, wherein said cyclic formal containing water is supplied to said reflux portion or upper stage of said distillation tower.

21. The method according to claim 17, wherein said distillate of said distillation tower is refluxed at least partially to said distillation tower, without discharging all of said distillate outside the system.

* * * * *

UNITED STATES PATENT AND TRADEMARK OFFICE
CERTIFICATE OF CORRECTION

PATENT NO. : 5,886,198
DATED : March 23, 1999
INVENTOR(S) : Ogawa et al.

It is certified that error appears in the above-identified patent and that said Letters Patent is hereby corrected as shown below:

In Column 16, line 9, please change "The method" to --A method--.

Signed and Sealed this

Twentieth Day of July, 1999

Attest:

Q. TODD DICKINSON

*Attesting Officer*  *Acting Commissioner of Patents and Trademarks*